(12) United States Patent
Takei

(10) Patent No.: US 12,127,994 B2
(45) Date of Patent: Oct. 29, 2024

(54) VIBRATION-GENERATING DEVICE

(71) Applicant: TAKET LLC, Fujisawa (JP)

(72) Inventor: Toshitaka Takei, Fujisawa (JP)

(73) Assignee: TAKET LLC, Kanagawa (JP)

( * ) Notice: Subject to any disclaimer, the term of this patent is extended or adjusted under 35 U.S.C. 154(b) by 295 days.

(21) Appl. No.: 17/618,087

(22) PCT Filed: Aug. 11, 2020

(86) PCT No.: PCT/JP2020/030556
§ 371 (c)(1),
(2) Date: Dec. 10, 2021

(87) PCT Pub. No.: WO2021/029401
PCT Pub. Date: Feb. 18, 2021

(65) Prior Publication Data
US 2022/0313547 A1 Oct. 6, 2022

(30) Foreign Application Priority Data
Aug. 14, 2019 (JP) .................................. 2019-148710

(51) Int. Cl.
*A61H 23/02* (2006.01)
*H10N 30/20* (2023.01)

(52) U.S. Cl.
CPC ..... *A61H 23/0245* (2013.01); *H10N 30/2023* (2023.02)

(58) Field of Classification Search
CPC ........ A61H 23/0245; A61H 2201/1604; A61H 2201/164; A61H 2201/165;
(Continued)

(56) References Cited

U.S. PATENT DOCUMENTS 3,816,774 A * 6/1974 Ohnuki ................. B06B 1/0688
310/369
6,135,969 A * 10/2000 Hale .................... A61B 5/4362
600/595
(Continued)

FOREIGN PATENT DOCUMENTS

JP 2005-125045 5/2005
JP 2005-185802 7/2005
(Continued)

OTHER PUBLICATIONS

Kobari JP2009148521 Translation (Year: 2009).*

*Primary Examiner* — Adil Partap S Virk
(74) *Attorney, Agent, or Firm* — Cozen O'Connor

(57) ABSTRACT

A piezoelectric band (10) includes: a base sheet (11) that has flexibility and is formed into a sheet shape; a piezoelectric sheet (20) that has flexibility and is formed into a sheet shape and placed over one side of the base sheet (11); and a cover sheet (12) that has flexibility and is formed into a sheet shape and placed over and in contact with one side of the piezoelectric sheet (20) that faces away from the base sheet (11). Upon reception of a drive signal, the piezoelectric sheet (20) vibrates at or above a frequency of 15 kHz. The cover sheet (12) has a plurality of holes (12a) passing therethrough from one side facing the piezoelectric sheet (20) to the other side, and the plurality of holes (12a) forms respectively air layers through which vibration of the piezoelectric sheet (20) propagates toward the other side.

9 Claims, 12 Drawing Sheets

(58) Field of Classification Search
CPC ........ A61H 2201/1654; A61H 2205/02; A61H 2205/027; A61H 2205/102; H10N 30/2023; H10N 30/857; H04R 17/025; H04R 2201/023; H04R 2460/13; A61N 2007/0078; A61N 7/00; A61N 7/022
See application file for complete search history.

(56) References Cited

U.S. PATENT DOCUMENTS

| | | | |
|---|---|---|---|
| 11,462,673 B2* | 10/2022 | Yoshida | G01L 1/16 |
| 2002/0156373 A1* | 10/2002 | Wakabayashi | B06B 1/0622 |
| | | | 600/437 |
| 2003/0135135 A1* | 7/2003 | Miwa | B06B 1/0688 |
| | | | 601/2 |
| 2004/0044298 A1* | 3/2004 | Kawabata | A61N 7/00 |
| | | | 601/3 |
| 2008/0243001 A1* | 10/2008 | Oakley | A61B 8/4281 |
| | | | 600/459 |
| 2009/0062656 A1* | 3/2009 | Hyuga | A61B 8/4488 |
| | | | 600/459 |
| 2010/0204583 A1* | 8/2010 | Rhim | A61B 8/00 |
| | | | 600/459 |
| 2011/0319766 A1* | 12/2011 | Tsuruno | A61B 8/04 |
| | | | 600/454 |
| 2015/0080771 A1* | 3/2015 | Barthe | A61N 7/02 |
| | | | 601/3 |
| 2015/0150533 A1* | 6/2015 | Nakamura | A61B 8/5207 |
| | | | 600/447 |
| 2017/0072225 A1* | 3/2017 | Maxwell | A61N 7/00 |
| 2017/0207729 A1* | 7/2017 | Kondoh | A41D 1/005 |
| 2020/0022670 A1* | 1/2020 | Eibl | A61B 8/4488 |
| 2021/0057633 A1* | 2/2021 | Ishiguro | B32B 7/025 |

FOREIGN PATENT DOCUMENTS

| | | | |
|---|---|---|---|
| JP | 2009-066459 | | 4/2009 |
| JP | 2009-148521 | | 7/2009 |
| JP | 2009148521 A | * | 7/2009 |
| JP | 4799798 | | 10/2011 |
| JP | 2017-035318 | | 2/2017 |
| JP | 2017-064273 | | 4/2017 |

* cited by examiner

VIBRATION-GENERATING DEVICE

PRIORITY CLAIM

This is a U.S. national stage of application No. PCT/JP2020/030556, filed on Aug. 11, 2020. Priority is claimed on the following application: Country: Japan, Application No.: 2019-148710, filed Aug. 14, 2019, the content of which is incorporated herein by reference.

TECHNICAL FIELD

This invention relates to technologies to generate and transfer vibration to a body of a person for therapy and/or the like.

BACKGROUND

In conventional ultrasound therapy equipment, a probe or an ultrasonic propagation medium coupled to an ultrasonic oscillator is placed into contact with the body in order to vibrates the body interior via the contact surface with the body (see Patent documents 1, 2). In this manner, such conventional ultrasound therapy equipment aims at producing heat within the body for improvement in blood circulation. Alternatively, conventional ultrasound therapy equipment produces ultrasonic vibration to perform a massage on a deep body site to activate cells.

CITATION LIST

Patent Documents

Patent document 1: Japanese Unexamined Patent Application Publication No. 2017-064273
Patent document 2: Japanese Unexamined Patent Application Publication No. 2005-185802

SUMMARY OF INVENTION

Technical Problem

The conventional ultrasound therapy equipment uses a hard probe as a member placed in contact with the body under therapy. For example, patent document 1 discloses a probe having a built-in ultrasonic oscillator near its distal end. The distal end portion of the probe to be placed in contact with the body is small in area in order for the vibration energy of the ultrasonic oscillator to be efficiently transferred to the body. Therefore, therapy coverage is confined due to a small contact area of the probe. Further, as a result of the hard distal end of the probe, the probe comes into point contact with a curved part of the body. This will impair the efficiency of transferring the vibration energy from the probe to the part in question.

To avoid this, it is conceivable that a gel medium is applied to either the distal end of the probe or the body, so that the efficiency of transferring the vibration energy is improved by interposing the gel medium between the distal end of the probe and the body. However, applying the gel medium requires time and effort, which is a cumbersome task.

Also, patent document 2 discloses apparatus for causing ultrasound energy to converge in air by using a focusing mirror to cover the distal end of a transmission line which is attached to an ultrasonic wave generator. However, the focusing mirror is bulky and hard to handle. Further, due to the structure of causing ultrasound energy to converge, the therapy coverage on the body is narrow.

Accordingly, it is an object of the present invention to enable more efficient transfer of vibration to a wide range of a body at a time.

Solution to Problem

To address to the problems, a first aspect of the present invention provides a vibration generating device that includes: a first sheet portion that has flexibility and is formed into a sheet shape; a piezoelectric portion that has flexibility and is formed into a sheet shape and placed over one side of the first sheet portion; and a second sheet portion that has flexibility and is formed into a sheet shape and placed over and in contact with one side of the piezoelectric portion that faces away from the first sheet portion. Upon reception of a drive signal, the piezoelectric portion vibrates at or above a frequency of 15 kHz. The second sheet portion has a plurality of paths passing therethrough from one side facing the piezoelectric portion to the other side, and the plurality of paths forms respectively air layers through which vibration of the piezoelectric portion propagates toward the other side.

In a second aspect of the present invention, the first sheet portion, the piezoelectric portion and the second sheet portion are preferably formed integrally into a flexible band shape and when he first sheet portion, the piezoelectric portion and the second sheet portion are bent into an arc shape, each of both ends of them extends to a position of 180 degrees or greater.

In a third aspect of the present invention, preferably, the piezoelectric portion and the second sheet portion are formed integrally into a concave and convex shape by sewing and have the sheet shape.

In a fourth aspect of the present invention, driving means configured to output the drive signal is preferably placed on one side of the first sheet portion that faces away from the piezoelectric portion.

In a fifth aspect of the present invention, the drive means preferably controls the drive signal based on at least one of a period of time during which the drive signal is continuously output, a starting time at which the drive signal is output, and an ending time at which the drive signal is output.

Advantageous Effects of Invention

According to the first aspect of the present invention, because the vibration generating device has flexibility as a whole, when being worn around a curved part of the body, the vibrating generating device is placed along and in close contact with the curved part to allow vibration of the piezoelectric portion to propagate to the body.

According to the first aspect of the present invention, because of the piezoelectric portion having the sheet shape, the vibration generating device causes vibration of the piezoelectric portion to propagate to the body with efficiency.

According to the first aspect of the present invention, the vibration generating device allows vibration of the piezoelectric portion to propagate through the air layers respectively formed by the plurality of paths.

According to the first aspect of the present invention, the vibration generating device enables propagation of vibration of the piezoelectric portion at or above a frequency of 15 kHz.

According to the second aspect of the present invention, when the first sheet portion, the piezoelectric portion and the second sheet portion are bent into an arc shape, each of both ends of them extends to a position of 180 degrees or greater. Therefore, if the vibration generating device is worn around a wide curved part of the body, the vibration generating device is placed along and in close contact with the curved part to allow the vibration of the piezoelectric portion to propagate to the body.

According to the third aspect of the present invention, the vibration generating device enables effective propagation of vibration of the piezoelectric portion as a result of the piezoelectric portion and the second sheet portion being integrally formed into a concave and convex shape by sewing, and having the sheet shape.

According to the third aspect of the present invention, for the vibration generating device, the concave and convex shape is formed by sewing, and thus the concave and convex shape is readily formed.

According to the fourth aspect of the present invention, the vibration generating device has the driving means, thereby being capable of operating while being carried.

According to the fifth aspect of the present invention, the vibration generating device controls the operation of the piezoelectric portion on the basis of time of day and time.

DESCRIPTION OF THE ILLUSTRATIVE EMBODIMENTS

Exemplary embodiments according to the present invention will now be described with reference to the accompanying drawings.

First Embodiment

A first embodiment is directed to an ultrasound output device.

Figure 1:
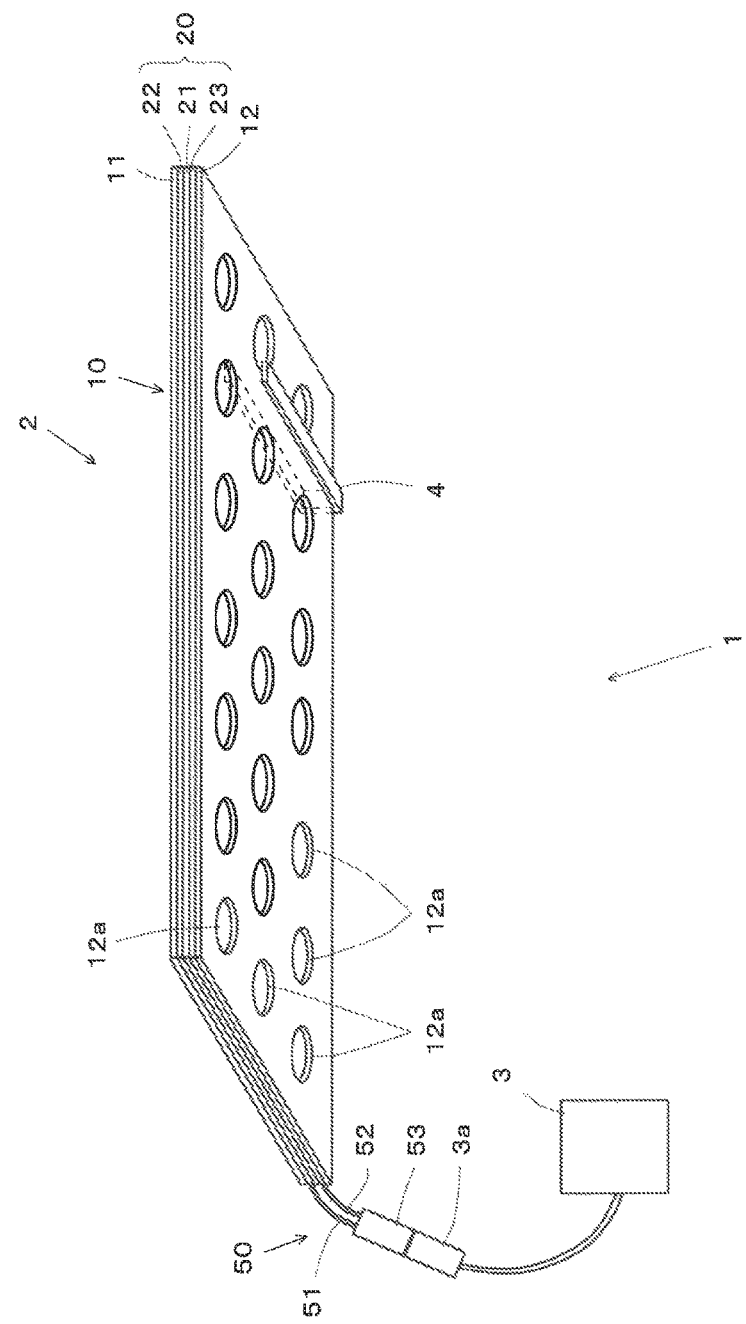
FIG. 1 is a diagram illustrating an example configuration of an ultrasound output device in accordance with a first embodiment.
Figure 2:
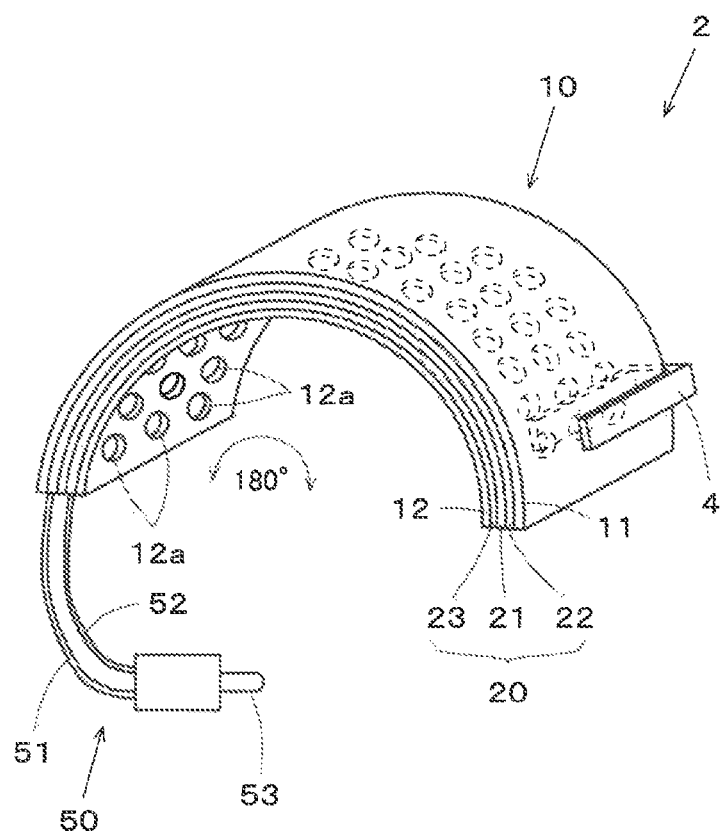
FIG. 2 is a perspective view illustrating an example of a bent piezoelectric band of the ultrasound output device in accordance with the first embodiment.

FIG. 1 is a diagram illustrating an example configuration of an ultrasound output device 1 in accordance with a first embodiment. FIG. 2 is a perspective view illustrating an example of a bent piezoelectric band of the ultrasound output device in accordance with the first embodiment.

As illustrated in FIG. 1, the ultrasound output device 1 has a piezoelectric device 2 and a drive unit 3. The piezoelectric device 2 has a piezoelectric band 10 and a connector 50. The piezoelectric band 10 is in the form of a sheet and has a rectangular shape (e.g., band shape) as a whole. The piezoelectric band 10 is formed by stacking a base sheet 11, a piezoelectric sheet 20 and a cover sheet 12 on top of another.

The base sheet 11 is formed of, for example, flexible materials. When the base sheet 11 is bent into an arc shape, the base sheet 11 is configured such that each of both ends in a long side direction extends to a position of 180 degrees or greater. The piezoelectric sheet 20 is placed over the base sheet 11.

The piezoelectric sheet 20 has a piezoelectric sheet main body 21, a first electrode layer 22 and a second electrode layer 23. The piezoelectric sheet 20 is structured with the piezoelectric sheet main body 21 sandwiched between the first electrode layer 22 and the second electrode layer 23.

The piezoelectric sheet main body 21 is a sheet member or a film member with a sheet shape or a film shape. The piezoelectric sheet main body 21 is a bendable polymer piezoelectric film such as, e.g., PVDF (Polyvinylidene fluoride resin) and the like. The first electrode layer 22 and the second electrode layer 23 are formed, for example, by a method of evaporating aluminum on both sides of the piezoelectric sheet main body 21, and/or the like. Thus, the piezoelectric sheet 20 has a sheet shape or a film shape as a whole. Here, the first electrode layer 22 and the second electrode layer 23 are electrically connected at their outer peripheral ends to the connector 50. The connector 50 is electrically connected to the first electrode layer 22 and the second electrode layer 23 using, for example, conductive adhesive and/or the like.

It is noted that ultrasonic oscillators are roughly classified into two, a rigid ceramic piezoelectric plate with electrodes formed on both sides of a ceramic substrate, and a bendable piezoelectric sheet with electrodes formed on both sides of a polymer piezoelectric film. For example, there is a film obtained by uniformly mixing powdery ceramic and/or the like with a substance with flexibility, and such a film with electrode layers deposited on both sides thereof may also be included as the piezoelectric sheet 20 in the embodiment. The cover sheet 12 is placed over the piezoelectric sheet 20 having such configuration.

The cover sheet 12 is formed of, for example, materials having breathability and flexibility. Examples of the breathable and flexible materials include cloth. The cover sheet 12 is formed with a plurality of holes 12a each having a predetermined shape and penetrating from one side to the other side of the cover sheet 12. The shape of each of the plurality of holes 12a is, for example, circular in shape.

As illustrated in FIG. 2, the piezoelectric band 10 having configuration as described above is highly flexible so that, when the piezoelectric band 10 is bent into an arc shape, each of both ends in the long side direction thereof extends to a position of 180 degrees or greater. Also, for the piezoelectric band 10, the base sheet 11, the piezoelectric sheet 20 and the cover sheet 12 are secured together into one piece with a pinch clip 4 or the like in order to maintain the integrity of the base sheet 11, the piezoelectric sheet 20 and the cover sheet 12.

The connector 50 has two cables, i.e., a first and second cables 51, 52, and a plug 53. The first cable 51 is electrically connected at one end to the first electrode layer 22 of the piezoelectric band 10. Also, the second cable 52 is electrically connected at one end to the second electrode layer 23 of the piezoelectric band 10. The other ends of the respective first and second cables 51, 52 are electrically connected to the plug 53.

The plug 53 is electrically connected to a jack 3a for connection to the drive unit 3. For example, the drive unit 3 is a function generator. The function generator is any commercially available function generator or the like. The drive unit 3 is able to output a drive signal (ultrasonic signal) at any frequency of the range of 15 kHz to 100 kHz. Here, the drive signal is a signal for driving the piezoelectric sheet 20 of the piezoelectric band 10. For example, a waveform of the drive signal is any of a sine wave, a square wave and a sawtooth wave or a waveform of a combination thereof.

Operation, Action and Others

The following description is of examples of operation, action and others of the ultrasound output device 1 according to the first embodiment. In the examples, the case of using the ultrasound output device 1 for therapy is described. Further, in the examples, the case of use to treat person's knee is described.

Figure 3:
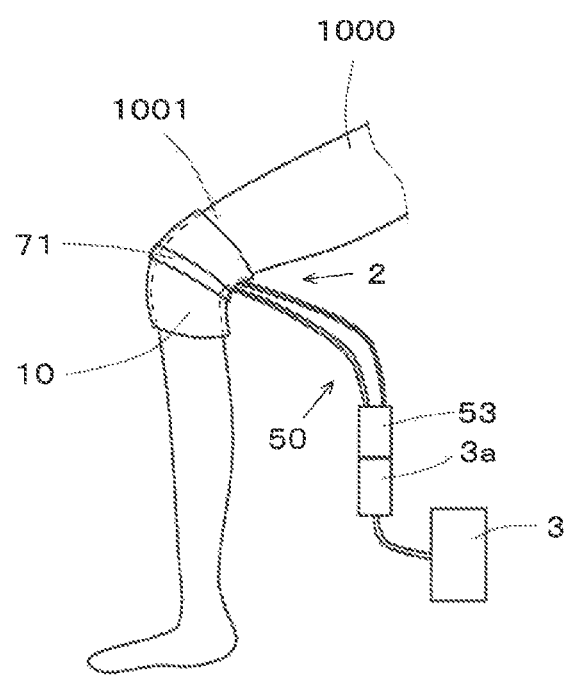
FIG. 3 is a diagram illustrating an example of a piezoelectric band worn around a knee.

FIG. 3 is a diagram illustrating an example of the piezoelectric band 10 worn around a knee.

As illustrated in FIG. 3, the piezoelectric band 10 is wrapped around a knee 1001 such that the cover sheet 12 faces the skin of a body 1000. Because the piezoelectric band 10 has flexibility as a whole, the piezoelectric band 10 is wrapped in close contact with the knee 1001 and along the outer periphery of the knee 1001. At this stage, when the base sheet 11 is bent into an arc shape, each of both ends in the long side direction extends to a position of 180 degrees or greater. As a result of this, when the piezoelectric band 10, viewed as a whole, is bent into an arc shape, each of both ends in the long side direction extends to a position of 180 degrees or greater.

Thus, the piezoelectric band 10 is wrapped along the outer periphery of the knee 1001 and in close contact with the knee 1001. Then, the piezoelectric band 10 is fixed to the knee 1001 from above by fixing means 71 such that the piezoelectric band 10 is secured to the knee 1001 with reliability. The fixing means 71 is, for example, a large rubber band or a hook-and-loop fastener. This further increases the adhesion of the piezoelectric band 10 to the knee 1001.

After that, the plug 53 of the piezoelectric device 2 is connected to the jack 3a of the drive unit 3. Then, the drive unit 3 is operated such that a drive signal (ultrasonic signal) at any frequency of the range of 15 kHz to 100 kHz is output to the piezoelectric sheet 20 of the piezoelectric device 2 from the drive unit 3.

Thus, the piezoelectric sheet 20 vibrates at any frequency of the range of 15 kHz to 100 kHz according to the drive signal from the drive unit 3. Then, the vibration is transferred as ultrasonic wave to the knee 1001 via air layers within the plurality of holes 12a penetrating the cover sheet 12. At this stage, the cover sheet 12 serves as a spacer between the body and the piezoelectric sheet 20, so that the distance between the body and the piezoelectric sheet 20 is maintained to a minimum while the vibration of the piezoelectric sheet 20 is transferred as ultrasonic wave to the knee 1001 at close range via air layers within the plurality of holes 12a penetrating the cover sheet 12. In this way, the ultrasound output device 1 is used for therapy for a person.

Further, while the ultrasound output device 1 was mounted to a person and the piezoelectric band was driven, the person listened to music. In this situation, the sound quality improvement effect of improving sound quality of the music the person listened to was obtained. The applicant believes with respect to such a result that the ultrasonic wave transferred to the body via the air layers within the holes 12a exert some influence on the whole body as well as on a mounting site for the piezoelectric band 10, so as to work to improve the sound quality of listened sound.

FIRST COMPARISON EXAMPLE

A piezoelectric band of a first comparison example will be described below for purposes of comparison with the embodiment.

Figure 4:
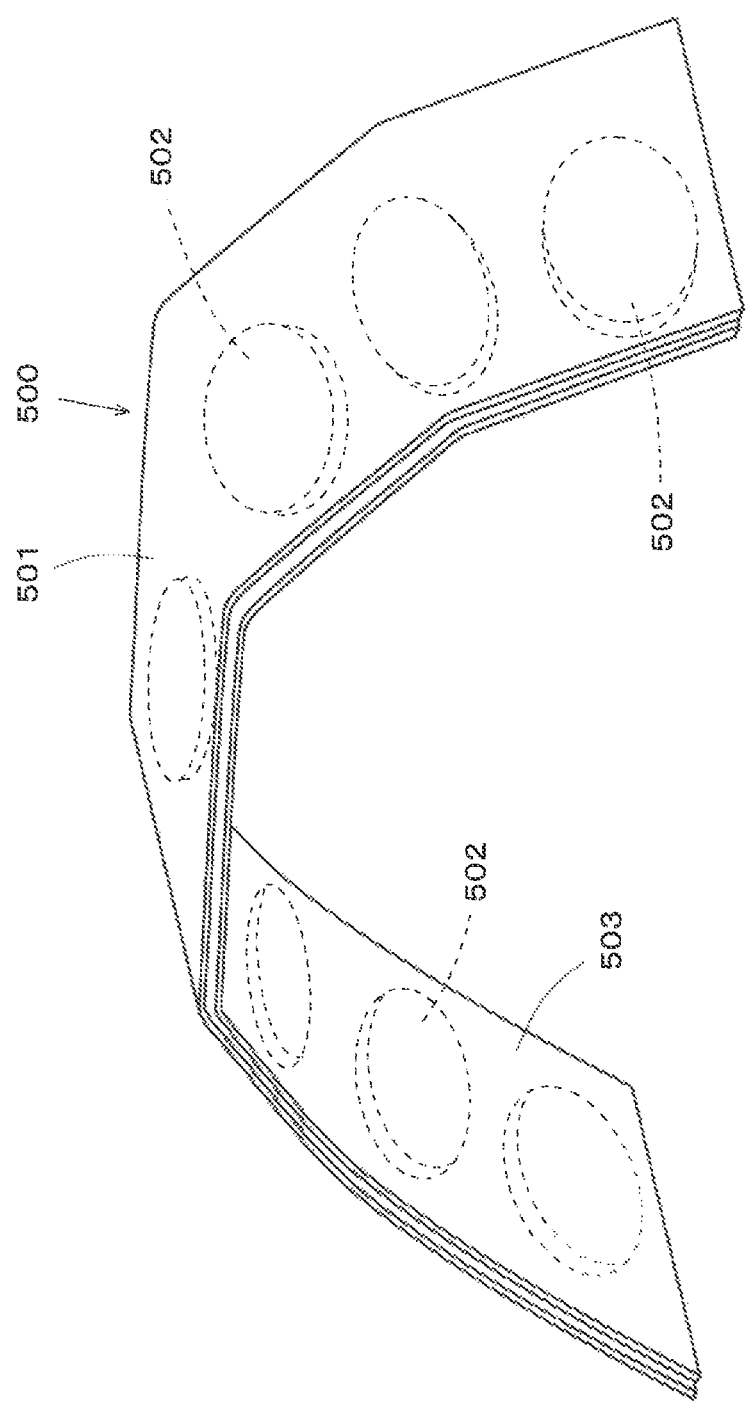
FIG. 4 is a diagram illustrating an example configuration of a piezoelectric band in accordance with a first comparison example.

FIG. 4 is a diagram illustrating an example configuration of a piezoelectric band 500 in accordance with the first comparison example.

As illustrated in FIG. 4, in the first comparison example, the piezoelectric band 500 is configured to stack a base sheet 501, a plurality of piezoelectric plates 502 made of ceramic, and a cover sheet 503. The plurality of piezoelectric plates 502 are conventional piezoelectric plates made of ceramic. Also, the plurality of piezoelectric plates 502 are individually affixed to the base sheet 501. The cover sheet 503 is mesh material with a plurality of meshes.

Figure 5:
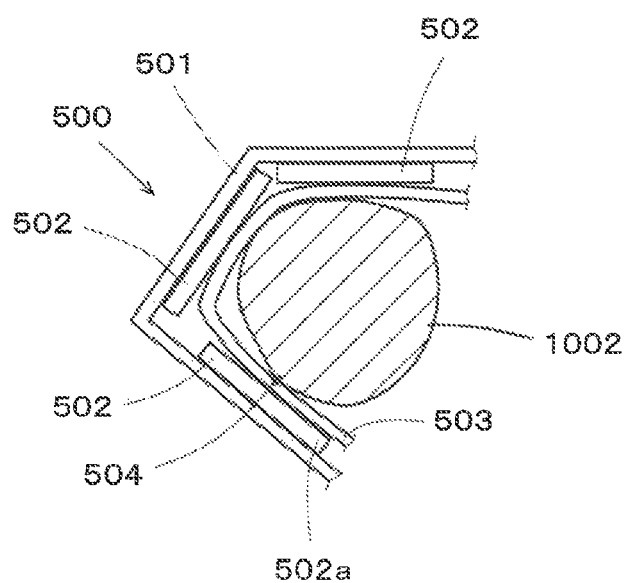
FIG. 5 is a sectional view illustrating the piezoelectric band in the first comparison example, the piezoelectric band being wrapped around an arm.

FIG. 5 is a sectional view illustrating the piezoelectric band 500 in the first comparison example, the piezoelectric band 500 being placed around an arm 1002 of a person.

As illustrated in FIG. 5, the piezoelectric plate 502 possess high rigidity, so that the piezoelectric plate 502 and the arm 1002 make approximate point contact at a point 504 via the cover sheet 503 with each other. At this stage, the vibration of the piezoelectric plate 502 propagates directly to the arm 1002, and therefore the vibration of the piezoelectric plate 502 propagates to the arm 1002 as mechanical vibration without change. On the other hand, a part 502a of the piezoelectric plate 502 is placed out of contact with the arm 1002 and located at a distance from the arm 1002, and vibration of the part 502a is radiated as sound wave to reach the arm 1002. However, because the sound wave is damped by the square of the distance, the sound wave is transferred to the arm 1002 in a very low intensity state.

In this connection, due to the difficulty of forming the ceramic piezoelectric plate to have a large area, the ceramic piezoelectric plate is used in a telephone sounding close to an ear, and the like. Also, due to high rigidity, the ceramic piezoelectric plate may transfer vibration directly to skin or bone. Therefore, the ceramic piezoelectric plate is also used in a bone conduction speaker which delivers a sound signal to an ear through a bone near an ear or a head.

In order to increase the transfer area from such ceramic piezoelectric plates, the use of a large number of ceramic piezoelectric plates is required. In turn, for use of a large number of ceramic piezoelectric plates, it is required to establish electric connection among the ceramic piezoelectric plates via lead wire. As described above, a variety of effort and time is required to increase the transfer area from the ceramic piezoelectric plates. Due to this, the application of devices or equipment using such ceramic piezoelectric plates is limited.

Where the equipment or device using a plurality of ceramic piezoelectric plates as described in the first comparison example is bent to be mounted to the body or the like for use, each of the ceramic piezoelectric plates is not bent, and therefore in view of the overall equipment or device, the mounting surface does not serve as a continuous vibration transfer surface. That is, each of the ceramic piezoelectric plates installed in the equipment or device comes into point contact with the mounting surface. Thus, the vibrations of the ceramic piezoelectric plates are transferred as discrete vibrations to the mounting surface.

For this reason, in the first comparison example, the strong mechanical vibration propagating from points 504 in point contact is predominant on the arm 1002, so that the vibration propagating as sound wave is very weak and canceled out by the mechanical vibration.

Further, the piezoelectric band 500 in the first comparison example was used to treat muscle soreness, tennis elbow and/or the like. However, no therapeutic effect was produced even when the vibration intensity of the piezoelectric plates 502 was increased. From the outcome of the therapy using the piezoelectric band 500 in the first comparison example, it is evident that the therapy using ultrasonic wave being transferred to the body via the air layers from the piezoelectric band 10 worn around the body as described in the aforementioned embodiment is distinct from the therapy using vibration transferred to the body from the piezoelectric plates 502 of the piezoelectric band 500 worn around the body as described in the first comparison example. On such results, the applicant believes with respect to the sound quality improvement effects according to the present invention that the sound quality improvement effect is produced by the same action of ultrasonic wave as sound wave on the biological body as the action when the therapeutic effect is produced by uniformly and widely transferring the vibration of the piezoelectric sheet 20 as ultrasonic wave via the air layers to the body at close range, the air layers being located within the plurality of holes 12a penetrating the cover sheet 12, as described in the embodiment.

It also is conceivable that bending the piezoelectric band is facilitated by arranging a plurality of piezoelectric plates (vibration plates) each smaller than the piezoelectric plate 502 in the first comparison example, for example, each piezoelectric plate of the order of a few centimeters to a few millimeters. However, in this case, a certain gap created between two of the plurality of piezoelectric plates is required in order to establish electric connection of the plurality of piezoelectric plates and/or to prevent contact between the piezoelectric plates. Hence, when the piezoelectric band is worn on the body, the gap areas where the piezoelectric plates are not placed do not vibrate, and this means the existence of wasted space in the piezoelectric band. Also, the existence of both of vibrating area and non-vibrating area in the single piezoelectric band leads to a reduction in therapeutic effect and sound quality improvement effect.

Further, a connection impedance may be produced between the plurality of piezoelectric plates and/or a plurality of physical constants may appear. This makes it difficult to vibrate all the plurality of piezoelectric plates in a similar fashion. As a result, uniform vibration of the entire piezoelectric band is made difficult.

On the other hand, the piezoelectric band 10 according to the first embodiment generates uniform vibration throughout the entire surface because the piezoelectric sheet 20 is formed of a sheet member of a single sheet shape. Further, the applicant has confirmed that the piezoelectric sheet 20 being a single sheet shaped sheet member is a key requirement for exerting the therapeutic effect and the sound quality improvement effect.

SECOND COMPARISON EXAMPLE

A piezoelectric band of a second comparison example will be described below for purposes of comparison with the embodiment.

Figure 6:
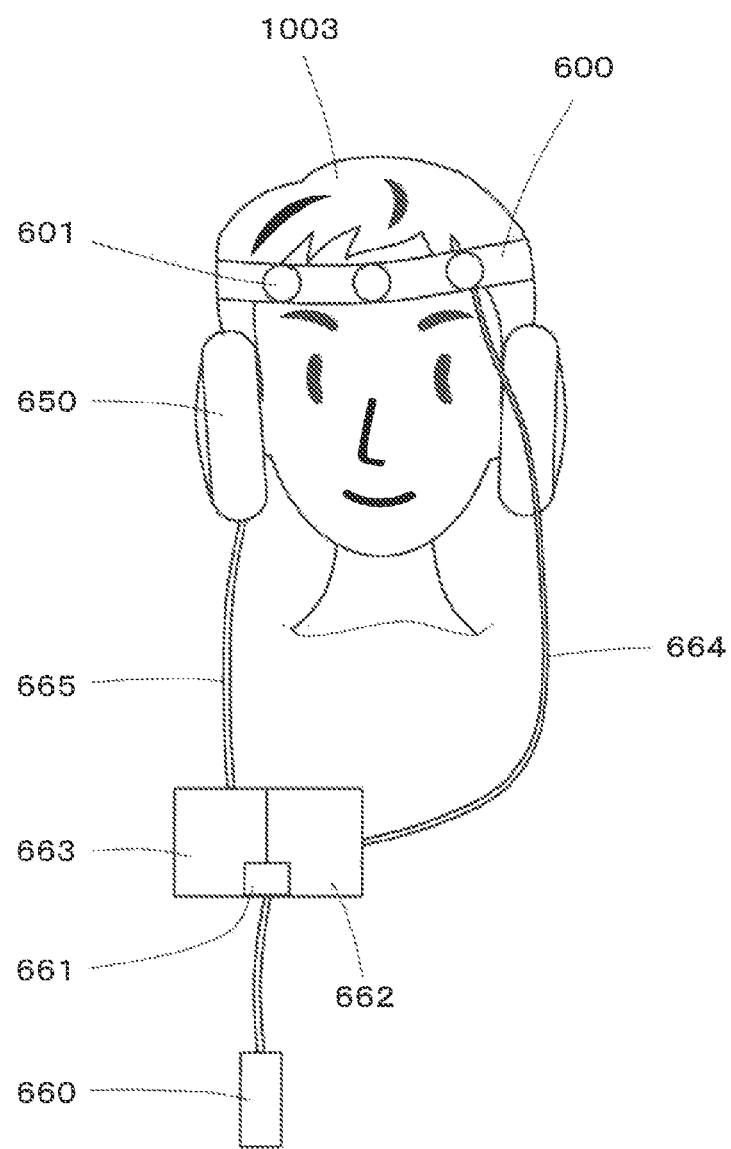
FIG. 6 is a diagram illustrating an example configuration of a piezoelectric band in accordance with a second comparison example.

FIG. 6 is a diagram illustrating an example configuration of a piezoelectric band 600 in accordance with the second comparison example.

As illustrated in FIG. 6, in the second comparison example, the piezoelectric band 600 has a plurality of piezoelectric plates 601 made of ceramic, and is used to be mounted around a head 1003, similarly to a bandana. And, in the second comparison example, the piezoelectric band 600 is used concurrently with a headphone 650 worn on ears. With such configuration, in the second comparison example, the headphone 650 and the piezoelectric plates 601 of the piezoelectric band 600 are simultaneously driven so that a signal from the piezoelectric plates 601 of the piezoelectric band 600 is mixed with an auricle signal of the sound heard directly by the ears from the headphone 650. In this stage, the signal from the piezoelectric plate 601 becomes a signal that transfers the mechanical vibration of the piezoelectric plate 601 to the auricles through the skull bone conduction. In this way, the sound quality is improved by mixing the signal from the piezoelectric plates 601 of the piezoelectric band 600 and the auricle signal of the sound heard directly by the ears from the headphone 650.

In the second comparison example, a music signal from a sound source apparatus 660 is input to a separator circuit 661, which is then split into amplifiers 662, 663 by the separator circuit 661 to be input to the piezoelectric band 600 and the headphone 650 through cables 664, 665, respectively.

A comparison is made between the second comparison example and the first embodiment. The piezoelectric band 600 in the second comparison example is configured using the ceramic piezoelectric plates 601. However, the piezoelectric band 10 in the embodiment is essentially composed of the flexible piezoelectric sheet 20. Because of such a difference in configuration, the second comparison example and the first embodiment differ in the principle of sound quality improvement from each other.

For example, the sound quality improvement was examined by mounting the piezoelectric band 600 in the second comparison example around/on a part of the body other than the head, which gave the result that the sound quality is not improved. On the other hand, the sound quality improvement was examined by mounting the piezoelectric band 10 in the embodiment around/on a part of the body other than the head, which gave the result that the sound quality is improved. With respect to such results, the applicant believes that vibration of the piezoelectric sheet 20 through the air layers within the plurality of holes 12a penetrating the cover sheet 12, is transferred as ultrasonic wave uniformly and widely to the body at close range, as described in the embodiment, and such transferring of the ultrasonic wave acts as therapeutic effect.

Also, as seen from the configuration illustrated in FIG. 6, the second comparison example and the aforementioned embodiment also differ in system for driving the piezoelectric band from each other.

THIRD COMPARISON EXAMPLE

A third comparison example will be described below for purposes of comparison with the embodiment.

The third comparison example is a piezoelectric sheet used such as in a sonorous poster and the like. And, the piezoelectric sheet in the third comparison example has electrodes formed on both sides of a piezoelectric sheet main body, and in turn the electrodes are coated with insulation to form a protective film.

When a piezoelectric sheet with such configuration is worn, e.g., on an arm of a body or the like, the protective film is interposed between the piezoelectric sheet main body and the body. In such a case, the vibration from the piezoelectric sheet main body is damped within the protective film, so that the vibration to be transferred to the body is smaller. Therefore, in the third comparison example, the therapeutic effect and the sound quality improvement effect are not produced.

Also, the film-shaped piezoelectric sheet has no rigidity, and therefore, upon contact with a different substance, the vibration of the film-shaped piezoelectric sheet is stopped. Thus, the vibration of the piezoelectric sheet is hard to be transferred to the different substance. Due to such an event, in the third comparison example, the therapeutic effect and the sound quality improvement effect may not be obtained. And, nonexistence of a cover sheet with holes makes the vibration hard to be transferred as sound wave to the body.

Advantageous Effects in the First Embodiment (1) Because the piezoelectric band 10 has flexibility as a whole, when the piezoelectric band 10 is worn around a curved part of a body, the piezoelectric band 10 is placed along and in close contact with the curved part to allow the vibration of the piezoelectric sheet 20 to propagate to the body.
(2) Because the piezoelectric sheet 20 has a sheet shape, in particular, a single sheet shape, the piezoelectric band 10 is capable of causing the vibration of the piezoelectric sheet 20 to propagate to the body with efficiency.
(3) The piezoelectric band 10 is capable of causing the vibration of the piezoelectric sheet 20 to propagate through the air layers within the plurality of holes 12a of the cover sheet 12 to the body. By virtue of this, the piezoelectric band 10 is capable of causing the vibration of the piezoelectric sheet 20 to propagate uniformly and widely to the body.
(4) The piezoelectric band 10 is capable of causing vibration at or above a frequency of 15 kHz to propagate to the body. The applicant carried out effect measurements at various frequencies, and obtained the result that vibration at or above a frequency of 15 kHz was more effective.
(5) When the piezoelectric band 10 is bent into an arc shape, each of both ends extends to a position of 180 degrees or greater. Therefore, when the piezoelectric band 10 is worn around a wide curved part of a body, it is placed along and in close contact with the curved part to allow the vibration of the piezoelectric sheet 20 to propagate as sound wave to the body.
(6) The piezoelectric sheet 20 of the piezoelectric band 10 is formed of a flexible member, and the degree of freedom in the shape of the piezoelectric band 10 is high. For example, the piezoelectric band 10 is capable of changing shape to conform the shape of a region to be treated, so that the treatable range undergoing a single therapy session may be extended to increase the therapeutic effect, and further the allowable level of applicability to various site to be treated is higher.

Second Embodiment

A second embodiment will now be described with reference to the accompanying drawings. It is noted that the description is given using like reference numbers/signs to indicate elements/configurations identical or similar to those in the above-described first embodiment.

Figure 7:
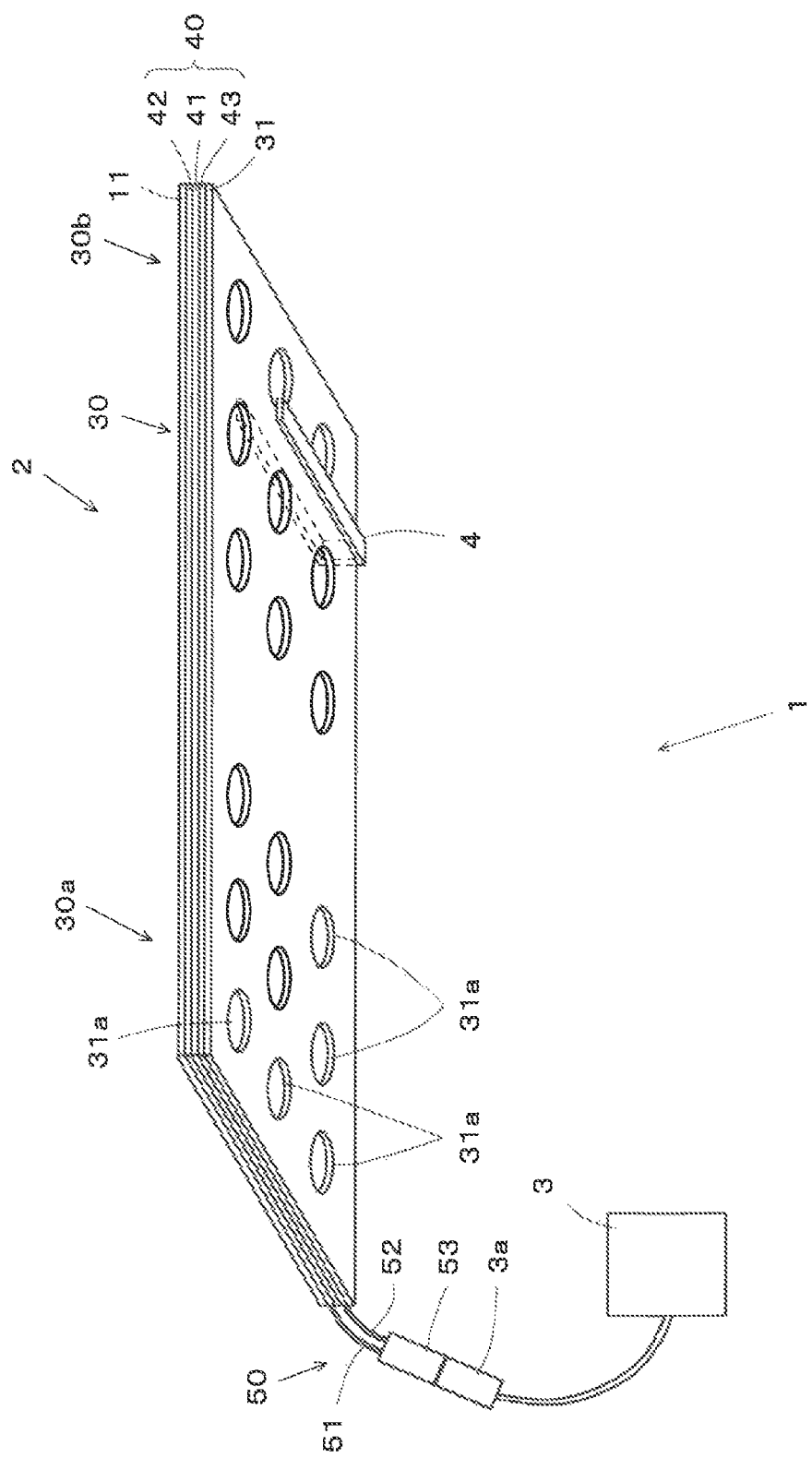
FIG. 7 is a perspective view illustrating an example configuration of a piezoelectric device in accordance with a second embodiment.

FIG. 7 is a perspective view illustrating an example configuration of a piezoelectric device 2 in accordance with the second embodiment.

As illustrated in FIG. 7, in the second embodiment, a piezoelectric band 30 is divided into a first piezoelectric band portion 30a and a second piezoelectric band portion 30b such that they are located both ends in the longitudinal direction of the piezoelectric band 30. Specifically, as in the case of the first embodiment, a piezoelectric sheet 40 is formed into a sheet shape or a film shape, and the piezoelectric sheet 40 is structured with a piezoelectric sheet main body 41 sandwiched between a first electrode layer 42 and a second electrode layer 43. The configuration of the first electrode layer 42 and the second electrode layer 43 is similar to that in the first embodiment, but the piezoelectric sheet main body 41 has a separation region formed in the vicinity of the longitudinal center thereof, the piezoelectric film being not formed in the separation region. Also, as in the case of the first embodiment, the first electrode layer 42 and the second electrode layer 43 are electrically connected to first and second cables (not shown) in the separation region of the piezoelectric sheet main body 41. Further, in the second embodiment, a plurality of holes 31a are formed in a cover sheet 31, and the plurality of holes 31a is grouped into and formed in both longitudinal ends of the piezoelectric band 30. With such configuration, the first piezoelectric band portion 30a and the second piezoelectric band portion 30b are formed separately in the piezoelectric band 30.

Operation, Action and Others

The following description is of examples of operation, action and others of the ultrasound output device 1 according to the second embodiment. In the examples, the case of using the ultrasound output device 1 to perform therapy on a person is described.

In the second embodiment, in the piezoelectric band 30, the first piezoelectric band portion 30a and the second piezoelectric band portion 30b are formed. And, because each of the first piezoelectric band portion 30a and the second piezoelectric band portion 30b has flexibility as a whole, when bending into an arc shape is performed, each of both ends in the long side direction extends to a position of 180 degrees or greater.

Figure 8:
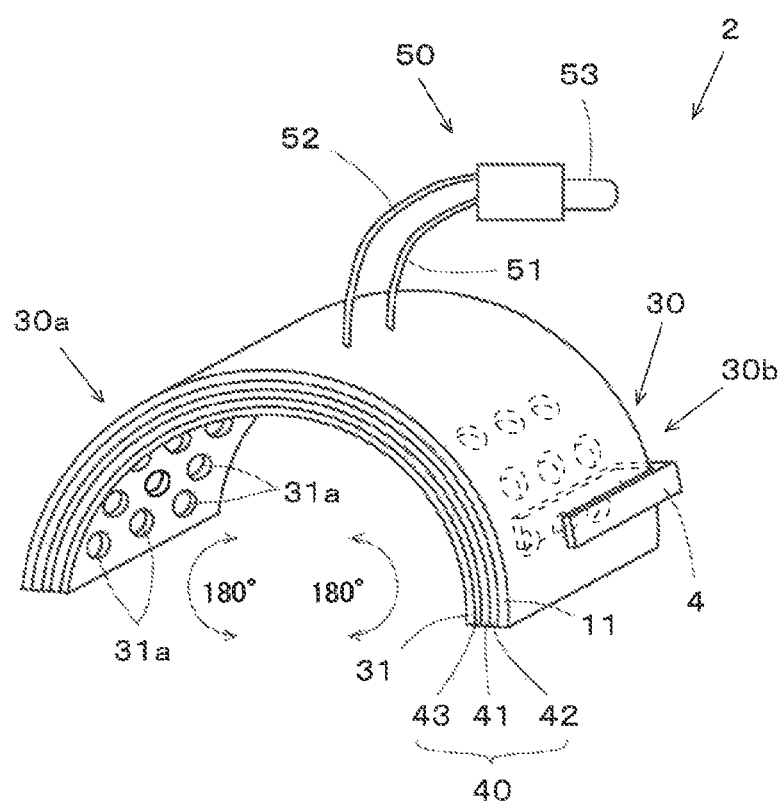
FIG. 8 is a perspective view illustrating an example of a bent piezoelectric band in accordance with the second embodiment.

FIG. 8 is a perspective view illustrating an example of the bent piezoelectric band 30 in accordance with the second embodiment.

As illustrated in FIG. 8, each of the first piezoelectric band portion 30a and the second piezoelectric band portion 30b extends until each end in the long side direction when the bending into an arc shape is performed reaches a position of 180 degrees or greater.

Here, for example, tennis elbow causes pain in the vicinity of upper and lower bones of an elbow. For therapy for such tennis elbow, the piezoelectric band 30 according to the second embodiment is wrapped from a lateral side of the elbow, and the respective ends of the first piezoelectric band portion 30a and the second piezoelectric band portion 30b of the piezoelectric band 30 extend to positions of 180 degrees or greater. Thus, the first piezoelectric band portion 30a is placed on the top of the elbow with reliability, and the second piezoelectric band portion 30b is placed on the bottom of the elbow with reliability.

And, upon activation by the drive unit 3, the first piezoelectric band portion 30a and the second piezoelectric band portion 30b vibrate at any frequency of the range from 15 kHz to 100 kHz. The vibration is transferred as ultrasonic wave to the elbow through the air layers within the plurality of holes 31a penetrating the cover sheet 31.

Advantageous Effects in Second Embodiment (1) When the bending into an arc shape is performed, each of both ends extends to a position of 180 degrees or greater. Because of this, when the first piezoelectric band portion 30a and the second piezoelectric band portion 30b of the piezoelectric band 30 are worn individually around a wide curved part of a body, they are placed along and in close contact with the curved part so that the vibrations of the first piezoelectric band portion 30a and the second piezoelectric band portion 30b are able to propagate to the body.

Third Embodiment

A third embodiment will now be described with reference to the accompanying drawings. It is noted that the description is given using like reference numbers/signs to indicate configurations identical or similar to those in the above-described first and second embodiments.

The third embodiment also discusses an ultrasound output device.

Figure 9:
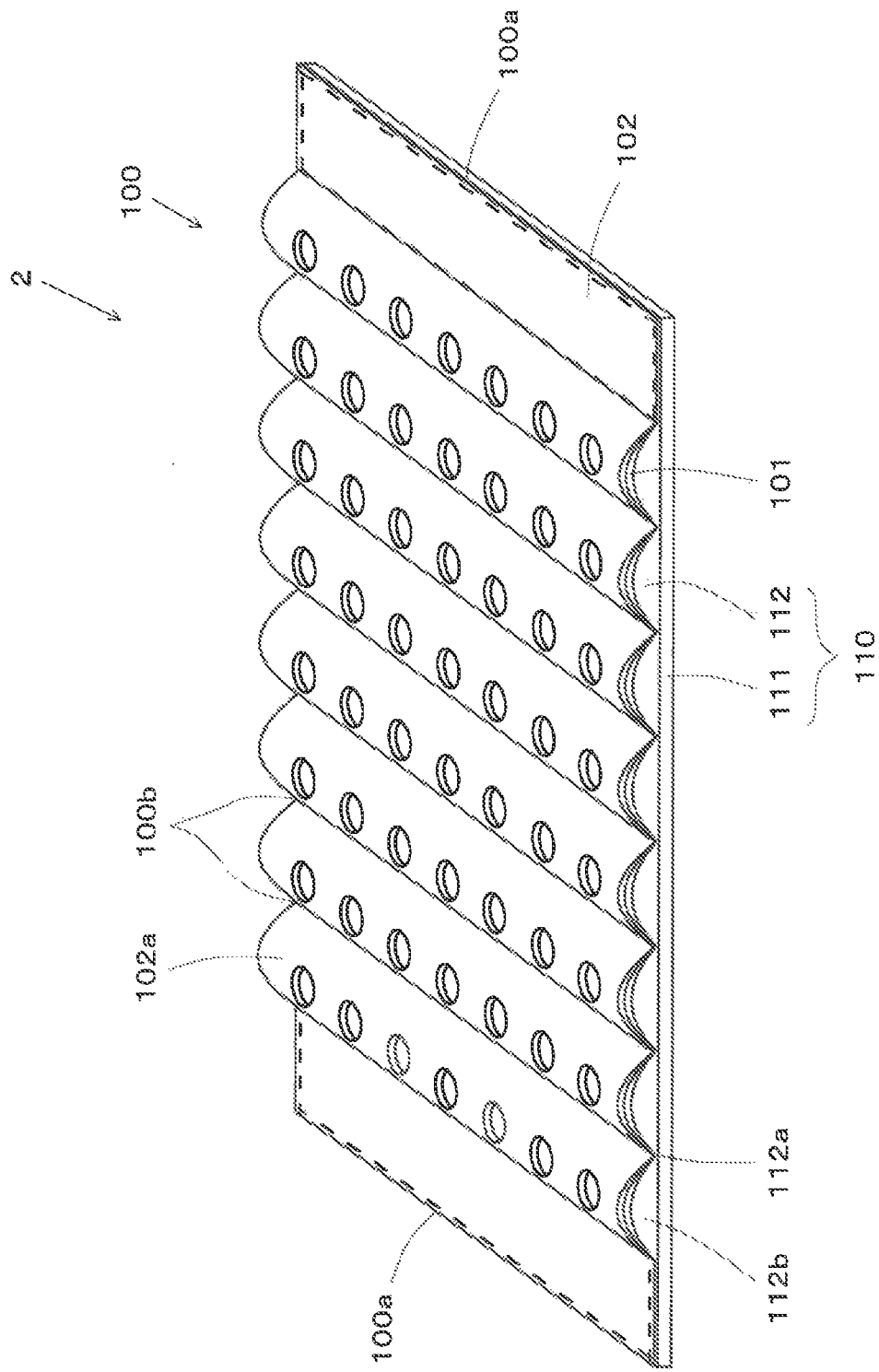
FIG. 9 illustrates an example configuration of an ultrasound output device in accordance with a third embodiment.

FIG. 9 illustrates an example configuration of an ultrasound output device 1 in accordance with the third embodiment.

As illustrated in FIG. 9, a piezoelectric band 100 in accordance with the third embodiment is formed by stacking a base sheet 110, a piezoelectric sheet 101 and a cover sheet 102 on top of another, similarly to the first embodiment. However, the piezoelectric band 10 in accordance with the third embodiment is formed by sewing the base sheet 110, the piezoelectric sheet 101 and the cover sheet 102 together with threads.

The base sheet 110 is formed of a composite material in which thick felt 112 is affixed onto cloth 111. For example, the cloth 111 is supple fabric exhibiting repulsion to a pressing force in the thickness direction.

Similarly to the first embodiment, the piezoelectric sheet 101 is structured with a piezoelectric sheet main body sandwiched between a first electrode layer and a second electrode layer.

The cover sheet 120 is formed of net-like materials. Examples of the net-like materials include a speaker net used in an audio speaker.

In the third embodiment, the base sheet 110, the piezoelectric sheet 101 and the cover sheet 102 are formed integrally, and a concave and convex shape is formed on the cover sheet 102 side. The concave and convex shape is formed as follows.

After the base sheet 110, the piezoelectric sheet 101 and the cover sheet 102 are stacked on top another, both longitudinal ends 100a are sewn with threads. And threads are used to sew zones 100b arranged at regular intervals in a ladder pattern in the longitudinal direction, so that the base sheet 110, the piezoelectric sheet 101 and the cover sheet 102 are sewn together. The treads are, for example, insulting threads.

Thus, in the felt 112, seam zones 112a are flattened and zones 112b adjacent to the seam zones 112a are not flattened to keep the shape. As a result, the total thickness of the base sheet 110, the piezoelectric sheet 101 and the cover sheet 102 being stacked on top of another is smaller in the suture portion than in other portions. Therefore, the shape obtained by stacking the base sheet 110, the piezoelectric sheet 101 and the cover sheet 102 on top of another has a convex cross section having an approximately semicircular shape in each part adjacent to the suture portions. This results in a concave and convex shape formed on the cover sheet 102 side as a whole. For example, the height of the convex portion is several millimeters, e.g., the order of 1 mm. Because of this, in visual appearance, the shape on the cover sheet 102 side of the piezoelectric band 100 is approximately flat.

Also, it is possible to form electrodes in the piezoelectric sheet 101 in a layout avoiding the suture portions. This enables the prevention of the electrodes in the piezoelectric sheet 101 from being damaged by the stitch passing through the electrodes. However, it has been confirmed that, even if the thread passes through the electrode, no short circuit has electrically occurred in a seam in the electrode, and therefore sewing may be carried out with the thread passing through the electrode without patterning. In this case, formation of electrodes is facilitated.

Operation, Action and Others

The following description is of examples of operation, action and others of the ultrasound output device 1 according to the third embodiment.

In the third embodiment, the piezoelectric band 100 has the concave and convex shape formed on the cover sheet 102 side. Thus, the piezoelectric band 100 is able to increase the ultrasonic waves propagating to the transfer surface through the air layers within the plurality of holes 102a penetrating the cover sheet 102.

Also, the concave and convex shape is readily formed by sewing. Further, the pattern of the concave and convex shape and the height of the convex portion are capable of being easily adjusted by simply adjusting the sewing position. As a result, the piezoelectric band 100 is adjust easily the output of the ultrasonic wave to propagate through the air layers within the plurality of holes 102a penetrating the cover sheet 102. Thus, for the piezoelectric band 100, it is possible to facilitate adjustment to maximize the output of ultrasonic waves at a desired frequency via the air layers within the plurality of holes 102a penetrating the cover sheet 102.

The applicant also has found that there are sizes of the concave and convex shape and shapes of the concave and convex portions in order to maximize the ultrasonic waves propagating through the air layers within the holes 102a. From this, it is possible to achieve a concave and convex shape which has the lowest possible height of the convex portion of the concave and convex shape while providing maximum ultrasonic waves propagating through the air layers within the holes 102a. In this way, when the piezoelectric band 100 is bent and worn around the body, the piezoelectric band 100 maintains its shape because of a small concave and convex shape, so that the ultrasonic waves propagating through the air layers within the holes 102a is kept maximal.

Advantageous Effects in Third Embodiment (1) The piezoelectric band 100 enables effective propagation of vibration of the piezoelectric sheet 101, as a result of the piezoelectric portion and the second sheet portion being integrally formed into a concave and convex shape by sewing, and having the sheet shape.
(2) The concave and convex shape is easily formed on the piezoelectric band 100 by sewing. And, because the concave and convex shape is easily formed by sewing, a concave and convex shape that maximize the effect produced by the ultrasonic waves may be readily formed on the piezoelectric band 100.
(3) For the piezoelectric band 100, the concave and convex portions are formed by sewing without the wasted space where no sound wave is radiated. This allows the vibration of the piezoelectric sheet 101 to propagate effectively.

Fourth Embodiment

A fourth embodiment will now be described with reference to the accompanying drawings. It is noted that the description is given using like reference numbers/signs to indicate configurations identical or similar to those in the above-described first to third embodiments.

The fourth embodiment also discusses an ultrasound output device.

Figure 10:
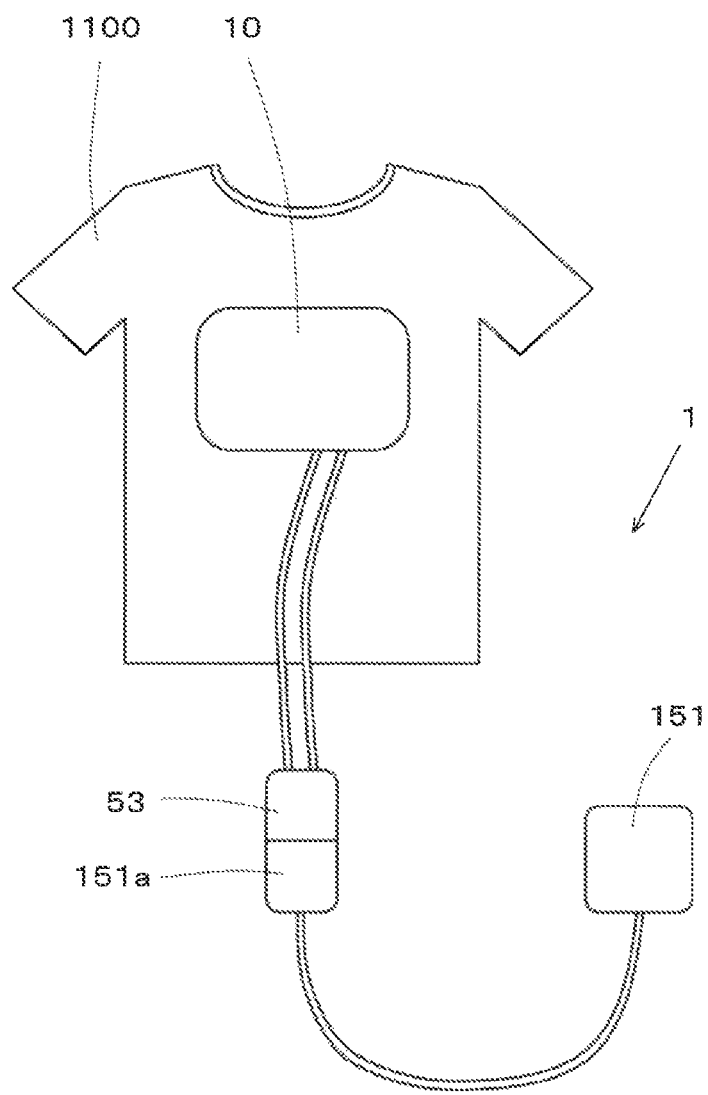
FIG. 10 is a diagram illustrating an example configuration of an ultrasound output device in accordance with a fourth embodiment.

FIG. 10 is a diagram illustrating an example configuration of the ultrasound output device 1 in accordance with the fourth embodiment.

As illustrated in FIG. 10, a drive unit 151 is a compact and lightweight device for portability. The drive unit 151 has a portion of the functionality of a function generator. Thereby, the drive unit 151 is capable of being operated by a compact electric cell or battery because of reduced functionality and operation in a power saving manner. Examples of the electric cell and battery include a single lithium ion battery and a single coin-type battery. Also, in the fourth embodiment, by insertion and removal between a plug 53 and a jack 151a on the drive unit 151 side, the electric connection between the piezoelectric band 10 and the drive unit 151 is turned on and off. On the other hand, the piezoelectric band 10 is configured such that, if for input of 15 kHz or greater, ultrasonic waves are sufficiently generated even at a voltage of 1V.

Operation, Action and Others

The following description is of examples of operation, action and others of the ultrasound output device 1 according to the fourth embodiment.

In the fourth embodiment, the piezoelectric band 10 is attached to closing such as a shirt 1100 or the like. For example, the piezoelectric band 10 is sewn on closing. In the fourth embodiment, because the drive unit 151 is compact and lightweight, this enables the user to carry the ultrasound output device 1 with the piezoelectric band 10 remaining attached to the shirt as described above.

Fifth Embodiment

A fifth embodiment will now be described with reference to the accompanying drawings. It is noted that the description is given using like reference numbers/signs to indicate configurations identical or similar to those in the above-described first to fourth embodiments.

The fifth embodiment discusses an ultrasound output device. The ultrasound output device in accordance with the fifth embodiment is a timepiece type ultrasound output device.

Figure 11:
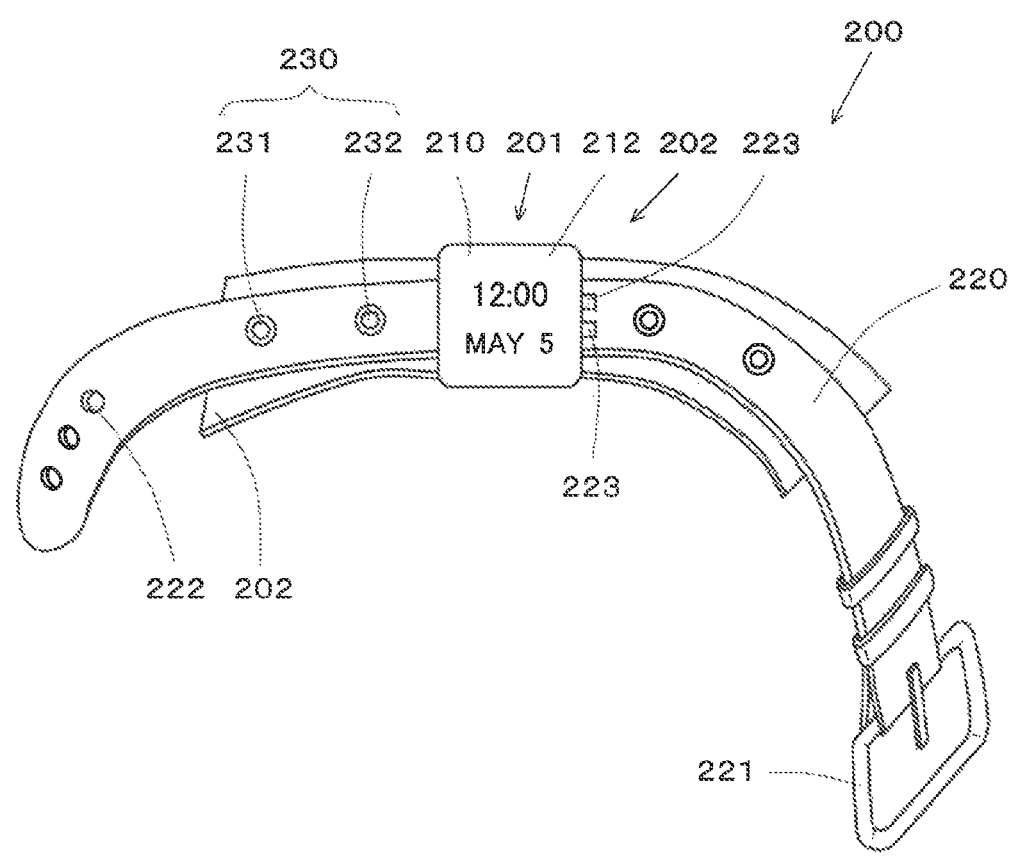
FIG. 11 is a diagram illustrating an example configuration of an ultrasound output device in accordance with a fifth embodiment.

FIG. 11 is a diagram illustrating an example configuration of an ultrasound output device 200 in accordance with the fifth embodiment.

As illustrated in FIG. 11, the ultrasound output device 200 is integral with a wristwatch. The ultrasound output device 200 has a wristwatch portion 201 and a piezoelectric band 202. The wristwatch portion 201 has a timepiece main body 210 and a strap portion 220.

Figure 12:
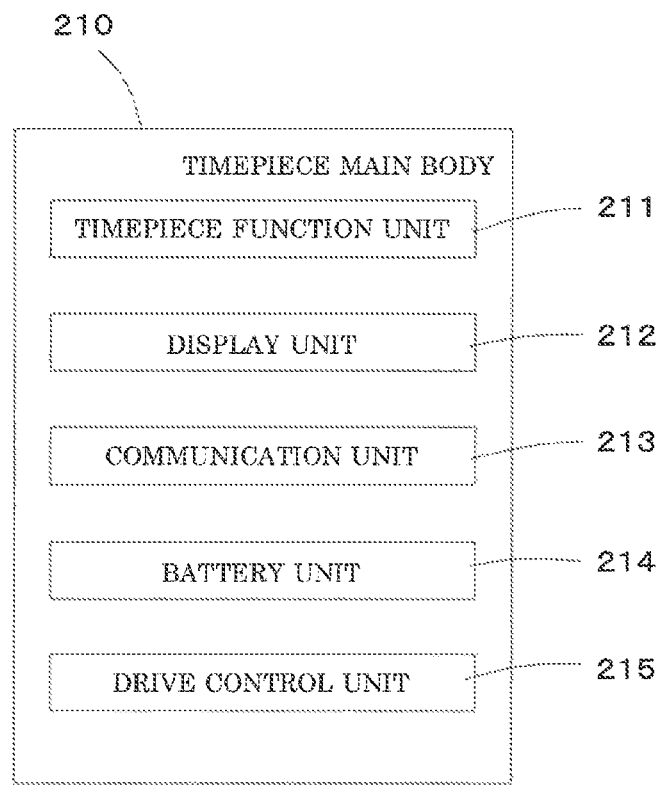
FIG. 12 is a diagram illustrating an example configuration of circuitry or functionality built in a timepiece main body in the fifth embodiment.

FIG. 12 is a diagram illustrating an example configuration of circuitry or functionality built in the timepiece main body 210 in the fifth embodiment.

As illustrated in FIG. 12, the timepiece main body 210 has a timepiece function unit 211, a display unit 212, a communication unit 213, a battery unit 214 and a drive control unit 215.

The timepiece function unit 211 has various timepiece functions including a timepiece, an alarm, a timer and/or the like. The display unit 212 displays information on timepiece and the like. The display unit 212 includes a touch panel which is externally operable. The communication unit 213 is a section for communication of the timepiece main body 210 with a different portable terminal such as a smartphone and the like. The timepiece main body 210 may establish communication with a different communication terminal through the communication unit 213 for operation in conjunction with the different communication terminal. The battery unit 214 serves as a power supply for driving the piezoelectric band 202. The battery unit 214 is, for example, a lithium-ion battery. The drive control unit 215 is connected to the battery unit 214 and powers and drives the piezoelectric band 202 while controlling the operation of the piezoelectric band 202 with a drive signal. For example, the drive control unit 215 produces the drive signal for control in response to the external operation performed on the display unit 212. Also, the drive control unit 215 is configured to be able to control in response to a request received from a different communication terminal via the communication unit 213.

The strap portion 220 is elongated and mounted with the timepiece main body 210 around the center of the front side. The strap portion 220 has one end at which a buckle 221 is mounted, and the other end in which a plurality of small holes 222 is formed, as in the case of a typical strap such as of a watch and the like. The piezoelectric band 202 is mounted on the backside of the strap portion 220. Also, on the strap portion 220, a timepiece side connector 223 is placed close to the timepiece main body 210.

The timepiece side connector 223 is electrically connected to the drive control unit 215 of the timepiece main body 210. A piezoelectric band side connector of the piezoelectric band 202, which will be described later, is detachably connected to the timepiece side connector 223.

The piezoelectric band 202 is formed in the form of a sheet and has a rectangular shape as a whole. For example, the length in the long side direction of the piezoelectric band ranges from 5 cm to 20 cm. The width in the short side direction of the piezoelectric band 202 ranges from 2 cm to 10 cm. As in the aforementioned first embodiment, the piezoelectric band 202 is formed by stacking a base sheet, a piezoelectric sheet and a cover sheet on top of another. The piezoelectric band 202 is placed along the strap portion 220 and around the center of the backside of the strap portion 220.

The piezoelectric band 202 is detachably attached to the strap portion 220 with snaps 230 as engageable means. In the example, two snap males 231 are placed on each of the opposite sides of the timepiece main body 210 on the strap portion 220. Correspondingly, four snap females 231 are placed on the piezoelectric band 202 and in the positions corresponding to the snap males 231. The piezoelectric band 202 is detachably attached to the strap portion 220 with the snaps 230 as described above. It should be noted that the number of snaps 230 may be a number other than 4.

The piezoelectric band 202 also has the piezoelectric band side connector which is not shown. The piezoelectric band side connector is electrically connected to the first electrode layer and the second electrode layer of the piezoelectric band 202. The piezoelectric band side connector is attachable to and detachable from the timepiece side connector 223 placed on the strap portion 220. The first electrode layer and the second electrode layer of the piezoelectric band are powered from the battery unit 214 with the piezoelectric band side connector engaged with the timepiece side connector 223.

Operation, Action and Others

The following description is of examples of operation, action and others of the ultrasound output device 200 according to the fifth embodiment.

First, the user of the ultrasound output device 200 uses the snaps 230 to attach the piezoelectric band 202 to the strap portion 220. The snaps 230 allow the user to attach the piezoelectric band 202 to the strap portion 220 with facility. Then, the user connects the piezoelectric band side connector of the piezoelectric band 202 to the timepiece side connector 223 of the strap portion 220. Thus, the piezoelectric band 202 becomes ready to be powered and driven.

In this manner, because the piezoelectric band 202 is configured to be attachable to and detachable from the strap portion 220, i.e., the wristwatch portion 201, the user removes the piezoelectric band 202 from the strap portion 220 in order to use the ultrasound output device 1 as a wristwatch usually. And, the user may attach the piezoelectric band 220 only when necessary for use as the ultrasound output device.

For wearing the ultrasound output device 200, the user wraps the strap portion 220 around his/her wrist, then adjust the length of the strap portion 220 by use of the buckle 221 and the small holes 222 of the strap portion 220 to fix the strap portion 220 to the wrist. In this stage, the length of the piezoelectric band 202 ranges from 5 cm to 20 cm, so that the piezoelectric band 202 surrounds the wrist of the user with an appropriate length. Because the length of the piezoelectric band 202 ranges from 5 cm to 20 cm, the piezoelectric band 202 is able to surround, with an appropriate length, the wrist of even a user such as, e.g., a child, a slender adult, an overweight adult. Also, because the width in the short side direction of the piezoelectric band 202 ranges from 2 cm to 10 cm, the user is not uncomfortable with the piezoelectric band 202 attached to the backside of the strap portion 220. Thus, the piezoelectric band 202 is in close contact with the user's wrist.

Then, the user operates the timepiece main body 210 and/or operates a smartphone which is a different communication device in communication with the timepiece main body 210, in order to activate the piezoelectric band 202 through the drive control unit 215. The user also may use the alarm function of the timepiece main body 210 to activate the piezoelectric band 202 at a preset time of day or to stop the piezoelectric band 202 under operating conditions at a preset time of day. The user also may use the timer function of the timepiece main body 210 to operate the piezoelectric band 202 for a preset period of time.

Thus, for example, the user may operate the piezoelectric band 202 during a time period when the user watches television. Specifically, the user may actuate the piezoelectric band 202 at the starting time of a television program to be watched and then may stop the operation of the piezoelectric band 202 at an ending time of the television program watched. Also, by virtue of such automated control of operation time, a reduction in power consumption of the ultrasound output device 200 is achieved.

Advantageous Effects in Fifth Embodiment (1) The ultrasound output device 200 has the drive control unit 215, thereby being capable of operating while being carried.
(2) The ultrasound output device 200 is able to control the operation of the piezoelectric band 202 based on time of day and/or a time period.
(3) The ultrasound output device 200 allows ultrasonic wave to propagate to a body of a wearer from the piezoelectric band 202 worn on his/her wrist. This makes it possible to improve the sound quality of sounds that are listened through cordless earphones or headphones by the wearer. Also, the applicant has carried out experiments under conditions where the piezoelectric band was mounted on/around various parts of a body, and achieved experimental results showing that the sound quality improvement effect was greatest when the piezoelectric band is worn around a wrist. The fifth embodiment provides an example based on such experiments.

It should be understood that, in the description of the above-described embodiments, the piezoelectric band essentially makes up, for example, a vibration generating device. Also, the base sheet essentially makes up, for example, a first sheet portion. Also, the piezoelectric sheet essentially makes up, for example, a piezoelectric portion. Also, the cover sheet essentially makes up, for example, a second sheet portion. Also, the holes essentially make up, for example, paths in which air layers are formed. Also, the drive control unit essentially makes up, for example, driving means.

Example Modifications Etc. of the Embodiments

In another example of the above-described embodiments, the piezoelectric band may be made up of any material(s) other than the above-described materials as long as the material(s) has flexibility. Also, on the shape, the piezoelectric band may be formed into any shape other than the above-described shapes.

In still another example of the above-described embodiments, the paths forming the air layers formed in the cover sheet may be formed into any shape other than the holes as long as the paths passing through the cover sheet from the frontside to the backside.

In yet another example of the above-described embodiments, the piezoelectric band may be configured to be operationally controlled to vibrate at or above a frequency of 20 kHz. For example, when the frequency of vibrations is less than 20 kHz, young people may be offended. On the other hand, if the vibration occurs at or above a frequency of 20 kHz, the frequency of vibrations falls outside the audible frequency range of human hearing, so that the sounds do not bother a person under therapy.

In another example of the first embodiment, the cover sheet 12 may be formed of meshed fabrics (may be cloth with a certain thickness). In this case, the plurality of holes 12a forms meshes.

In another example of the second embodiment, the holes 31a in the cover sheet 31 may not be divided into two and formed in both longitudinal ends of the piezoelectric band 30, and instead may be formed throughout the cover sheet 31.

In another example of the third embodiment, the base sheet 110 may not be formed of the composite material in which the thick felt 112 is affixed onto the cloth 111, and instead may be formed of a single material. In this case, for example, sewing may be performed while making wrinkles on the cover sheet side to form the concave and convex shape on the cover sheet side.

In another example of the third embodiment, the base sheet 110, the piezoelectric sheet 101 and the cover sheet 102 are stacked and sewn in specific patterns such as a ladder pattern or the like, but instead may be sewn randomly. In this case, the concave and convex shape is also formed on the base sheet 110 side.

In another example of the fourth embodiment, in the ultrasound output device 1, the piezoelectric band 10 and the drive unit 151 may be electrically connected to each other without the intervention of the jack and the plug. In this case, for example, the drive unit 151 has a switch for turning on/off operation.

In another example of the fourth embodiment, the shirt 1100 itself may be designed as a piezoelectric band. In short, the shape of the piezoelectric band according to each of the first to fifth embodiments is not limited as long as the effects are exerted.

The embodiments according to the present invention have been disclosed and it should be apparent to those skilled in the art that a modification and a change can be made without departing from the sprit and scope of the present invention. Such all modifications and equivalents are intended to be embraced within the scope of the appended claims.

INDUSTRIAL APPLICABILITY

The piezoelectric band having bendability and small thickness and outputting ultrasonic wave from the wide area is available for wearable use. Therefore, there is a prospect of providing simple and convenient use not only at home but also for business use such as in a medical facility and the like. Further, in the audio field, the piezoelectric band can be used as a device for improving a sound field and sound quality and a device for making sound clear when a television is watched.

REFERENCE SIGNS LIST

1 ultrasound output device
2 piezoelectric device
10, 30, 100 piezoelectric band
11, 110 base sheet
20, 40, 101 piezoelectric sheet
12, 31, 102 cover sheet
12a, 31a hole
215 drive control unit

What is claimed is:

1. A vibration generating device for delivering ultrasound to a wearer's body, comprising:
   a base sheet portion that has flexibility and is formed into a sheet shape;
   a piezoelectric portion that has flexibility and is formed into a sheet shape and stacked with the base sheet portion so that a first side of the piezoelectric portion is in contact with a side of the base sheet; and
   a cover sheet portion that has flexibility and is formed into a sheet shape and stacked with the piezoelectric portion so that a first side of the cover sheet portion is in contact with a second side of the piezoelectric portion opposite the first side and a second side of the cover sheet portion is configured to be placed in contact with the wearer's body, wherein
   upon reception of a drive signal, the piezoelectric portion vibrates at or above a frequency of 15 kHz, and
   the cover sheet portion has a plurality of paths passing therethrough from the first side of the cover sheet portion facing the piezoelectric portion to the second side of the cover sheet portion, and the plurality of paths from respective air layers through which vibration of the piezoelectric portion propagates toward the second side of the cover sheet portion.

2. The vibration generating device according to claim 1, wherein the base sheet portion, the piezoelectric portion and the cover sheet portion are formed integrally into a bendable band shape and when the base sheet portion, the piezoelectric portion and the cover sheet portion are bent into an arc shape, each of both ends of them extends to a position of 180 degrees or greater.

3. The vibration generating device according to claim 2, wherein the piezoelectric portion and the cover sheet portion are integrally formed into a concave and convex shape with respect to the base sheet by sewing and have the sheet shape.

4. The vibration generating device according to claim 2, further comprising a drive unit configured to output the drive signal at a frequency of the range of 15 kHz to 100 kHz.

5. The vibration generating device according to claim 4, wherein the drive unit configured to output the drive signal is placed on one side of the base sheet portion that faces away from the piezoelectric portion.

6. The vibration generating device according to claim 1, wherein the piezoelectric portion and the cover sheet portion are integrally formed into a concave and convex shape with respect to the base sheet by sewing and have the sheet shape.

7. The vibration generating device according to claim 1, further comprising a drive unit configured to output the drive signal at a frequency of the range of 15 kHz to 100 kHz.

8. The vibration generating device according to claim 7, wherein the drive unit controls the drive signal based on at least one of a period of time including a starting time at which the drive signal is output, and an ending time at which the drive signal is output.

9. A wristwatch, comprising:
   a main body;
   a strap portion; and
   the vibration generator according to claim 1, the vibration generator configured such that a side of the base sheet portion opposite the piezoelectric portion is adjacent to the main body so that the cover sheet portion is configured to be adjacent to the wearer's body; and
   the piezoelectric portion is powered and driven by a battery part for driving a timepiece built in the main body.

* * * * *